United States Patent [19]

Salem

[11] Patent Number: 5,011,489
[45] Date of Patent: Apr. 30, 1991

[54] ENDOTHELIUM STRIPPER AND METHOD OF USING THE SAME

[75] Inventor: Mohamed E. M. Salem, Moharem Bake, Egypt

[73] Assignee: University of South Florida, Tampa, Fla.

[21] Appl. No.: 417,534

[22] Filed: Oct. 5, 1989

[51] Int. Cl.$^5$ ............................................. A61B 17/00
[52] U.S. Cl. ...................................................... 606/159
[58] Field of Search ............... 606/106, 159, 170, 161; 128/757, 758

[56] References Cited

U.S. PATENT DOCUMENTS

| D. 237,116 | 10/1975 | Ekbladh. | |
|---|---|---|---|
| D. 282,965 | 3/1986 | Wellenstam. | |
| 2,779,334 | 1/1957 | Sandborn. | |
| 2,863,458 | 12/1958 | Modny et al. | |
| 3,635,223 | 1/1972 | Klieman | 606/194 |
| 3,659,606 | 5/1972 | Reimels. | |
| 3,741,214 | 6/1973 | Tillander. | |
| 4,528,982 | 7/1985 | Wellenstam. | |

FOREIGN PATENT DOCUMENTS

| 953597 | 8/1974 | Canada. | |
|---|---|---|---|
| 208154 | 1/1987 | European Pat. Off. | 128/785 |
| 395076 | 1/1974 | U.S.S.R. | |
| 1242126 | 7/1986 | U.S.S.R. | |

OTHER PUBLICATIONS

Surgery vol. 55, #6, 6-1964, p. 812.
Sklar Surgical Instruments p. 120 (1984).
Alde Medical 1965, p. 45.
Armed Forces Journal p. 1525, 10-1953.
Surgery vol. 27, p. 281, Issue No. 2, 2-1950.
162 Jama Oct. 20, 1956, p. 729-730.
"In Situ Bypass Grafting", The Origin and Evolution of an Elegant Technique (1987), Le Maitre.

*Primary Examiner*—Michael H. Thaler
*Attorney, Agent, or Firm*—Joseph C. Mason; Ronald E. Smith

[57] ABSTRACT

A surgical tool for stripping the endothelium from varicose veins. A smooth probe member surmounts an elongate flexible wire and is inserted into the vein and withdrawn therefrom as a preparatory step. The smooth probe member is then removed from the wire member, and a smooth head member of frusto conical configuration is then mounted to the distal end of the wire. A plurality of barbed head members are then secured to the smooth head member, in longitudinal alignment with one another, distal to the smooth head member. The head members can be rigidly or flexibly interconnected to one another. The barbs on the barbed head members are swept back to facilitate their insertion into the vein and such barb members engage and strip the endothelium when the head members are withdrawn from the vein. The smooth head member is the leading head member during such withdrawal.

16 Claims, 3 Drawing Sheets

ENDOTHELIUM STRIPPER AND METHOD OF USING THE SAME

TECHNICAL FIELD

This invention relates, generally, to surgical tools. More particularly, it relates to a tool that removes the inner lining of varicose veins without removing the veins from the patient's body.

BACKGROUND ART

Varicose veins are usually found in the limbs of the lower body; they are veins that are abnormally dilated and elongated.

Various surgical treatments have been developed to treat the condition; these treatments include removal of the affected veins from the body.

For example, in 1846, Brodie advised ligation of the long sapheous trunk above large varices in the thigh; this was confirmed by Trendelenberg in 1890.

Thereafter, in 1906, Mayo described high ligation and external stripping of the great saphenous vein from the groin to the knee and excision therebelow. Babcock, in 1907, described high ligation of the internal saphenous and saphenectomy from the groin to the knee and excision below the knee.

Dodd and Oldham, in 1940, performed varicose vein operations by dividing the saphenofemoral and saphenopopliteal unions and injecting a sclerosant distally in the saphenous trunk. However, Boyd pointed out in 1952 that sclerosants should not be administered unless the patient can be immediately active and moving after the operation.

A flexible stripper for vein removal after proximal ligation was disclosed by Myers in 1954.

U.S. design Pat. Nos. 237,116 and 282,965 show surgical tools having utility in the removal of varicose veins. Moreover, U.S. utility Pat. Nos. 2,779,334, 2,863,458, 3,659,606, 3,741,214, and 4,528,982 show surgical tools having utility in removing veins as well.

Canadian patent No. 953,597, Russian patent Nos. 395,076, 1,242,126, and E.P. patent No. 208,154 are also of interest.

Non-patent publications which form a part of the prior art include volume 27 of Surgery magazine at page 281, 10 Armed Forces Journal 1525, 162 JAMA (Oct. 20, 1956), 55 Surgery 812, Aloe Medical 1965, page 45 and Sklar 1984, page 120.

There are numerous problems with surgical removal of varicose veins. For example, the post operative recovery period can be long and painful. Moreover, post operative hemorrhages are not uncommon. Other complications include saphenous neuritis or avulsion. Drug treatments also have the severe limitations pointed out above.

Accordingly, the art is in need of a treatment of the condition that does not involve surgical removal of the veins and which does not rely upon the administration of drugs. However, the prior art neither teaches nor suggests what treatment that might be.

DISCLOSURE OF INVENTION

The present inventive surgical tool is new, useful and nonobvious in view of the prior art; it treats the condition of varicose veins without surgical removal of the vein and requires no drug therapy. Since surgical removal is avoided, the patient's recovery is faster, less painful and substantially free of post-operative complications such as hemorrhages, avulsion and the like.

The novel surgical tool is slidably inserted into the vein to be treated; when the tool is withdrawn, it strips the inner lining from the vein while leaving the vein in place and thus successfully treats the condition.

The tool includes an elongate flexible wire member having a handle at a first or proximal end thereof to facilitate manipulation of the wire. A plurality of stripper members, or head members, are positioned in longitudinally spaced relation to one another at the distal end of the wire. Each head member is frusto-conical in configuration and the leading or distal end of each head member is slightly larger in diameter than its trailing or proximal end. Moreover, the diameter of the heads increases from the most proximal end to the most distal end thereof. The most proximal of the head members is smooth but the distal heads are barbed; the barbs are swept back to allow facile insertion of the head members into the vein to be treated. When the heads are retracted from the vein, the barbs engage the inner lining of the vein and strip it off.

In a first embodiment, the heads are spaced from one another by rigid spacer members; in a second embodiment, the head members are spaced from one another by flexible wire interconnector members.

In both embodiments, a smooth probe member is inserted into the vein and withdrawn therefrom preparatory to insertion of the head members.

It is therefore understood that a primary object of this invention is to provide a surgical tool and method for treating varicose veins in the absence of surgical removal of said veins.

More particularly, an important object of this invention is to provide a tool that strips the inner lining from varicose veins.

Additional objects will become apparent as this description proceeds.

The invention accordingly comprises the features of construction, combination of elements and arrangement of parts that will be exemplified in the construction set forth hereinafter and the scope of the invention will be set forth in the claims.

DESCRIPTION OF THE DRAWINGS

For a fuller understanding of the nature and objects of the invention, reference should be made to the following detailed description, taken in connection with the accompanying drawings, in which.

Similar reference numerals refer to similar parts throughout the several views of the drawings.

BEST MODES FOR CARRYING OUT THE INVENTION

Figure 1:
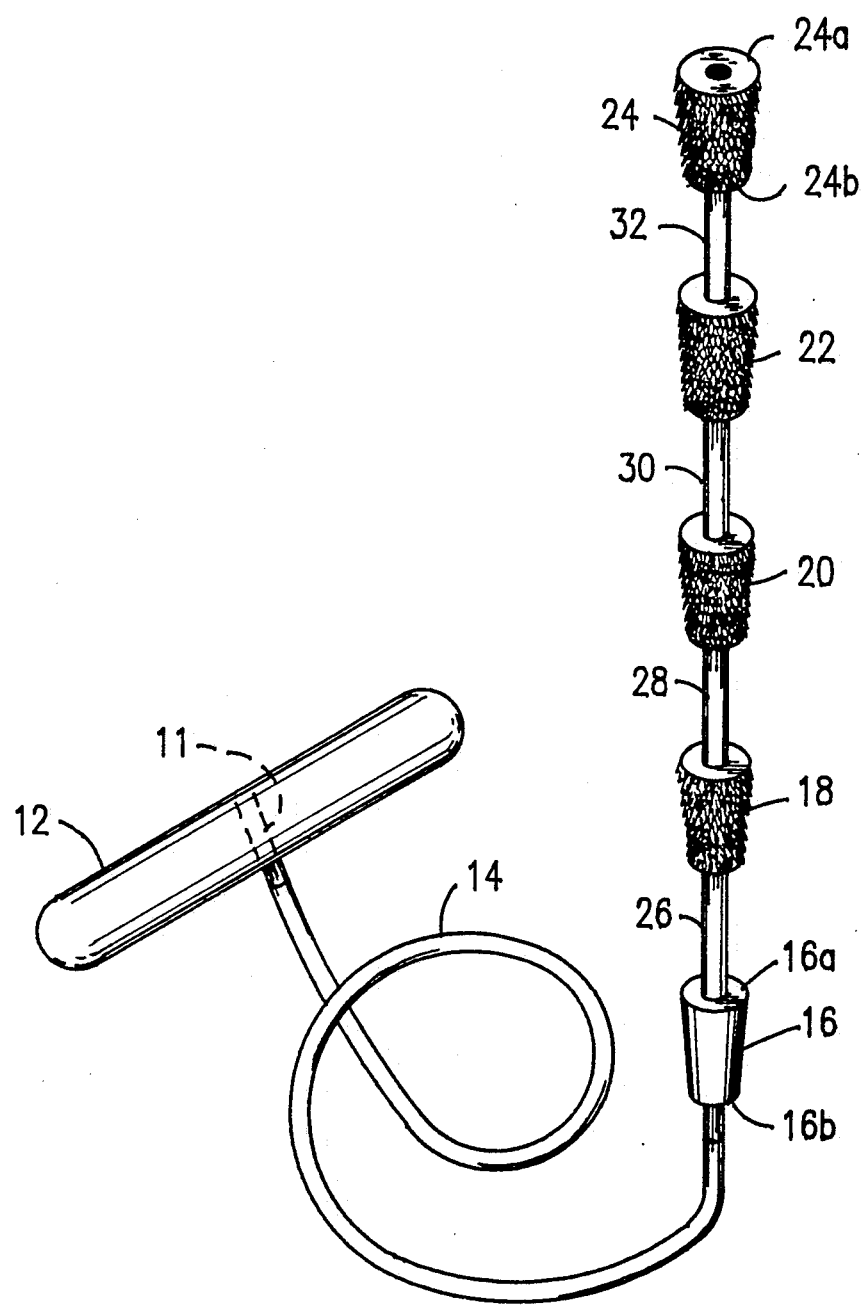
FIG. 1 is a perspective view of a first embodiment of the invention in its assembled configuration.

Referring now to FIG. 1, it will there be seen that an illustrative embodiment of the present invention is denoted by the reference numeral 10 as a whole.

Surgical tool 10 includes handle member 12, elongate flexible wire 14, first head member 16, second head member 18, third head member 20, fourth head member 22 and fifth head member 24.

For purposes of this description, the term "proximal" or "trailing" will indicate the handle end of device 10 and the term "distal" or "leading" will indicate the opposite end thereof. Thus, the fifth head member 24 is the most distal of the head members and the first head member 16 is the most proximal.

In a first embodiment of the invention, head members 16, 18, 20, 22 and 24 are longitudinally spaced apart from one another by rigid spacer members 26, 28, 30 and 32.

Figure 2:
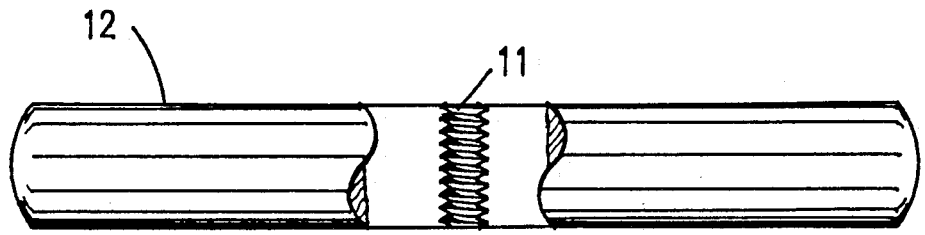
FIG. 2 is an elevational view of the handle member shown in FIG. 1.
Figure 3:
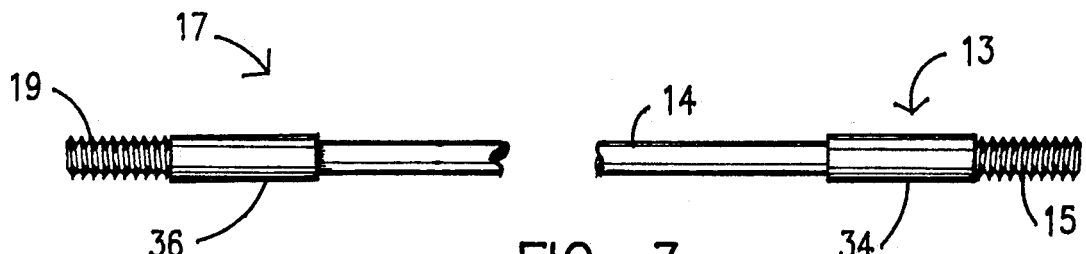
FIG. 3 is a side elevational view of the wire member shown in FIG. 1.

Handle member 12 is shown in increased detail in FIG. 2; it includes an internally threaded, transversely disposed bore means 11. As perhaps best understood in connection with FIG. 3, the proximal end 13 of wire 14 carries an externally threaded screw member 15 that screw threadedly engages the internally threaded bore 11 of handle 12.

More particularly, screw member 15 axially extends from and is integral to ferrule member 34 which slidably receives said proximal end 13 of wire 14 and which securely retains said wire therein against retraction therefrom.

Similarly, the distal end 17 of wire 14 is slidably received within distal ferrule 36 and externally threaded screw member 19 is integral to said ferrule 36 and projects axially therefrom.

Figure 4:
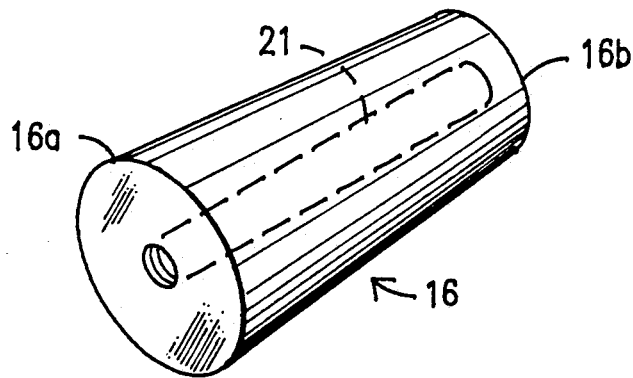
FIG. 4 is a perspective view of the smooth head member.

The first head member 16, shown in increased detail in FIG. 4, is axially bored as at 21; its distal end is denoted 16a and its proximal end is denoted 16b. The diameter of distal end 16a is preferably about seven mm. and the diameter of proximal end 16b is preferably about four mm. Head 16, like the other four head members, has flat ends and as such is of frusto-conical configuration as shown. For reasons that will become clear as this description proceeds, head 16 has a smooth outer surface.

The proximal end 16b of internally threaded bore means 21 screw threadedly receives externally threaded screw member 19 which is disposed at the distal end of wire 14 as aforesaid.

Figure 5:
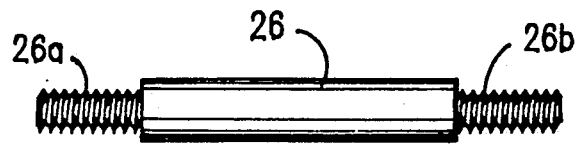
FIG. 5 is a side elevational view of a spacer member of the type shown in FIG. 1.

Rigid spacer member 26, shown in increased detail in FIG. 5, has externally threaded screw members 26a, 26b axially projecting from its opposite ends as shown in said FIG. 5. Screw member 26b screw threadedly engages the distal end 16a of bore means 21 of first head member 16. Screw member 26a of spacer 26 engages an internal bore means 23 (FIG. 6) formed in second head member 18.

Figure 6:
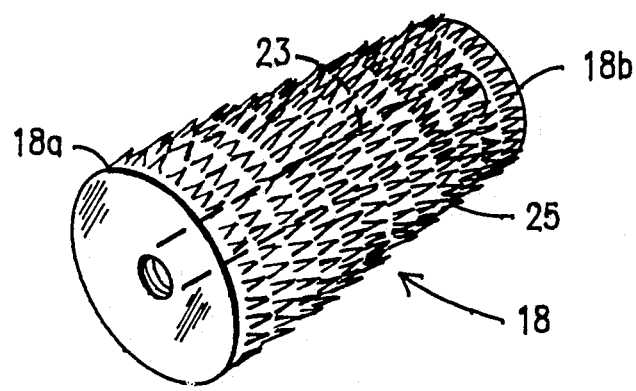
FIG. 6 is a perspective view of a barbed head member.

As best shown in FIG. 6, head member 18, like head member 16, is also of frusto-conical configuration. Its distal end 18a is preferably about 8 mm. in diameter and its proximal end 18b is preferably about 5 mm. in diameter.

The surface of head member 18 is substantially covered with a plurality of swept backed barb members, collectively denoted 25. In a preferred embodiment, the angle of sweep is about 15 degrees and the height or length of each barb is about 0.5 mm. The barbs are swept back in a distal-to-proximal direction to enable facile insertion of the head members when the inventive tool 10 is used in the manner hereinafter described.

Spacer members 28, 30 and 32 have the same structure as spacer members 26 and head members 20, 22 and 24 are respectively screw threadedly engaged to said spacer members in the manner just described.

The diameter of the proximal end of third head member 20 is 6 mm. and the diameter of the distal end thereof is 9 mm.

The diameter of the proximal end of fourth head member 22 is 7 mm. and the diameter of the distal end thereof is 10 mm.

The diameter of the proximal end of the fifth head member 24 is 8 mm. and the diameter of its distal end is 11 mm.

Figure 7:
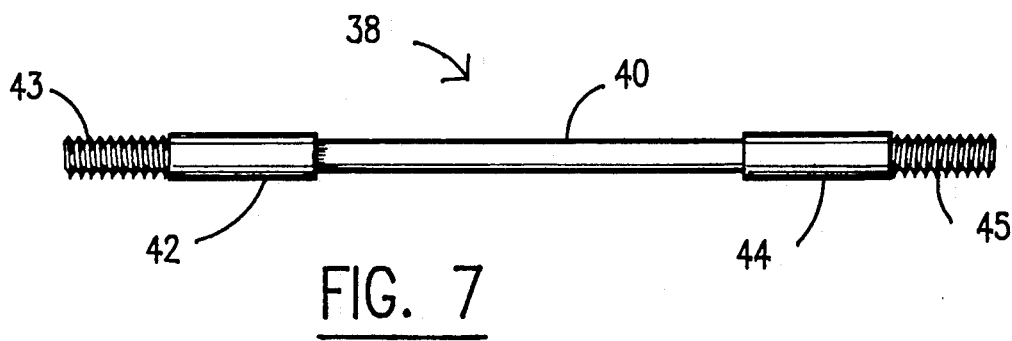
FIG. 7 is a side elevational view of a flexible interconnector member that interconnects the head members in lieu of the rigid spacer member of FIG. 5.

Thus, it should now be clear that the head assembly depicted in FIG. 1 is a rigid assembly and is suitable for use with many patients. However, where a patient's veins are substantially tortuous, a non-rigid interconnecting member is provided for interconnecting the head members; said non-rigid interconnecting means is shown in FIG. 7 and is denoted 38 as a whole.

Member 38 includes a wire member 40 having ferrule members 42, 44 at its opposite ends; externally threaded screw members 43, 45 are integral to said ferrule members and project axially therefrom as shown. Said screw members 43, 45 screw threadedly engage the internal bores of the respective head members in the same manner as the screw members that project from the rigid spacer members described earlier. In this manner, the head members are flexibly interconnected.

Figure 8:
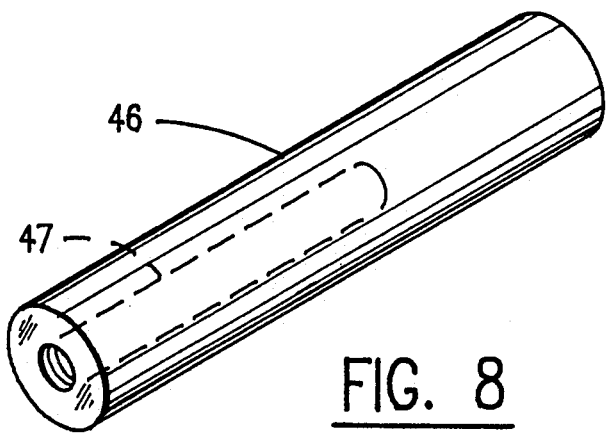
FIG. 8 is perspective view of the probe member of this invention.

A final part of the novel structure is shown in FIG. 8 and is denoted 46 as a whole. Probe member 46 has an internally threaded bore 47 formed therein as shown. The use of probe member 46 is perhaps best understood in connection with FIG. 3; externally threaded screw member 19 at the distal end 17 of wire 14 is screwed threadedly engaged with the internally threaded bore 47 formed in probe 46 at the beginning of the stripping procedure, i.e., probe 46 is engaged to screw member 19 prior to the attachment of the head members to tool 10.

More particularly, the novel procedure begins with the attachment of smooth probe member 46 to screw member 19. Probe member 46 is then slidably introduced into the vein to be stripped; the flexibility of wire 14 enables it to be inserted as far as the physician deems advisable. Wire 14 and probe 46 at the distal end thereof is then fully retracted from the vein by pulling on handle 12.

The probe 46 is then removed from screw member 19 and the first head member 16 is engaged to screw member 19 as earlier described, and the rest of the head assembly is put together in either of the two manners described hereinabove, i.e., either with the rigid spacer members of FIG. 5 or the flexible interconnecting members of FIG. 7 and the head members are inserted into the vein, head member 24 being the leading head member. Again, the amount of insertion is determined by the physician. The number and size of head members is also determined by the physician. The swept back orientation of the barbed members 25 makes the insertion easy. Once the insertion is complete, the physician withdraws the head members from the vein by manipulating handle 12; barbs 25 engage the inner lining (endothelium) of the vein and strips it off. Thus, the endothelium is removed from the vein when the tool 10 is withdrawn but the vein remains in place.

Smooth head member 16 is the trailing head member during the insertion procedure but it becomes the leading head member during the withdrawal procedure. Its smooth outer surface serves to dilate the vein and centralize the heads. Its frusto-conical configuration is advantageous for the same reason.

The novel surgical tool is used in an operation the steps of which are also novel; a more detailed description of the novel method follows.

In preparation for the surgery, the patient is placed in a supine position and general or spinal anesthesia is administered. The thigh and knee are slightly in flexion and external rotation.

The operation begins with a six cm. incision in the femoral skin crease. The lateral end of the incision is over the femoral pulse. The superficial fascia is incised, thereby exposing, at the center of the incision, the proximal part of the saphenous trunk and most of its tributaries. The adventicia of the saphenous trunk is then incised longitudinally and separated from the vein all around, thereby exposing various tributaries and facilitating dissection proximally to the sapheno-femoral junction. The vein is then transected between hemostats and the proximal segment is mobilized to its junction with the common femoral vein. All tributaries are divided and ligated during said dissection. The proximal stump of the saphenous trunk is doubly ligated with a proximal free tie and is then transfixed by suture ligation of silk. The other end of the saphenous trunk is dissected distally until a large medial superficial femoral cutaneous tributary is exposed. That tributary is divided and ligated if it is close.

A second incision is then made, about one to two cm. above and anterior to the medial malleollus. The incision is about two cm. in length and may be transverse or longitudinal. A pair of mosquito hemostats are then employed to grasp the edges of the transected lower end of the saphenous trunk. A one cm. slit is made in the trunk to facilitate the insertion of the probe end of the tool.

The novel instrument is gently advanced in a proximal to distal direction, i.e., it is carefully inserted into the patient's vein. The physician guides the tool with palpating, advancing fingers. In most cases, the smooth probe member can be advanced through the entire extent of the vein. The lesser saphenous vein can then be stripped if indicated; major varicose tributaries identified and marked before the operation are segmentally stripped or excised.

The probe member 46 is then removed and replaced by the head members 16, 18, 20, 22 and 24 which are either rigidly interconnected to one another as described in the first embodiment hereof, or flexibly interconnected as described in the second embodiment. For example, the rigid interconnections are advisable in tubular varices, flexible interconnections are best employed in large tortuous varices, and combinations of rigid and flexible interconnections may be employed in some cases, depending upon the shape of the varicosities. All five head members are not employed in all cases; any head member having a leading end diameter greater than the size of the vein lumen is removed. The tool is manipulated gently until all head members enter the lumen of the vein. The insertion is facilitated by small (one to two cm) longitudinal slits made in the vein wall. A double ligature closes the upper end of the vein and the femoral incision is closed as well.

The tool is then pulled downwardly. The spikes or barbs 25 formed thereon abrade the intima into small fragments and sweeps it down through the distal wound. The surgeon, using a free hand, enhances the abrading and scrubbing process by pressing on the head members from the exterior. An assistant compresses the vein with a rolled towel for about five minutes during the closure of the ankle wound. The limb is then wrapped snugly within a layer of cotton gauze and compression elastic bandages are wrapped thereover from the base of the toes to the groin. Post operative care includes a fifteen degree elevation of the limb and early ambulation. The original dressings are removed after forty eight hours and the compression elastic bandages are reapplied until the stitches are removed.

An elastic stocking is worn by the patient for six weeks after the operation. Residual varices, which may appear in three weeks in cases of large tributaries, and irregular small varices, which may appear in six weeks, are managed by sclerotherapy, although such irregular small varices may disappear spontaneously after proximal control of the main saphenous vein trunk.

Clearly, this invention represents a major breakthrough in the art of varicose veins treatment; it pioneers the art of fine-surgical treatment of such veins and for that reason the claims that follow are entitled to broad interpretation, so as to protect the heart of the invention, as a matter of law.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A surgical tool for removing the endothelium of a vein, comprising:
    an elongate, flexible wire member having a proximal end and a distal end;
    a head member, of frusto conical configuration, disposed at and fixedly secured to the distal end of said wire member; and
    a distal end of said head member having a diameter greater than the diameter of a proximal end thereof;
    a plurality of barb members formed on an outer surface of said head member;
    said barb members being swept back at a predetermined angle to facilitate insertion of the head member into a vein;
    whereby retraction of said wire member and said head member strips the endothelium from said vein.

2. The tool of claim 1, wherein the diameter of the distal end of said head member is about 11 mm. and wherein the diameter of the proximal end thereof is about 8 mm.

3. The tool of claim 1, wherein said barb members are swept back at an angle of about fifteen degrees.

4. The tool of claim 1, further comprising an internally threaded axial bore means formed in said head member.

5. The tool member of claim 1, further comprising a handle member fixedly secured to a proximal end of said wire member.

6. The tool of claim 1, wherein said barb members are about one-half mm in length.

7. A surgical tool, comprising:
- an elongate, flexible wire member having a leading end and a trailing end;
- a plurality of longitudinally spaced head members, each of which has a frusto conical configuration, being positioned at the leading end of said wire member;
- a leading end of each of said plurality of head members having a diameter greater than its trailing end;
- at least one of said head members having a plurality of barb members formed on an outer surface thereof;
- at least one of said head members having a smooth outer surface; and
- said at least one head member having a smooth outer surface being disposed at a trailing end of said plurality of head members.

8. The tool of claim 7, wherein the diameter of the leading end of each head member is greater than the diameter of the leading end of a head member disposed in trailing relation thereto.

9. The tool of claim 8, wherein the diameter of the trailing end of each head member is greater than the diameter of the trailing end of a head member disposed in trailing relation thereto.

10. The tool of claim 9, wherein said plurality of head members includes five head members, four of which have barbs formed on their respective outer surfaces and one of which has a smooth outer surface.

11. The tool of claim 10, wherein the barbs formed on the outer surface of the barbed head members are swept back in a leading-to-trailing direction to facilitate insertion of the head members into a vein.

12. The tool of claim 11, wherein said barbs have a substantially uniform extent of about one-half mm.

13. A method of stripping the endothelium from a vein, comprising the steps of:
- slidably inserting a head member of frusto conical configuration having swept back barb members formed on an outer surface thereof into said vein;
- slidably inserting a smooth, barbless head member of frusto conical configuration into said vein subsequent to insertion of said barbed head member;
- inserting the barbed and barbless head members into said vein with their respective larger diameter ends preceding their respective smaller diameter ends so that said larger diameter ends follow the smaller diameter ends thereof during withdrawal of said barbed and barbless head members from the vein;
- retracting said barbless head member and said barbed head member from said vein;
- whereby said barb members do not engage the inner lining of the vein during their insertion thereinto due to the swept back orientation of said barb members; and
- whereby said barb members engage and strip the inner lining from said vein when said barbed head member is withdrawn therefrom.

14. The method of claim 13, further comprising the step of interconnecting a plurality of barbed head members to one another and slidably inserting all of said interconnected barbed head members into said vein prior to the step of inserting said barbless head member.

15. The method of claim 14, further comprising the step of rigidly interconnecting said plurality of barbed and barbless head members to one another.

16. The method of claim 14, further comprising the step of flexibly interconnecting said plurality of barbed and barbless head members to one another.

* * * * *